(12) United States Patent
Sachs

(10) Patent No.: US 9,745,140 B2
(45) Date of Patent: Aug. 29, 2017

(54) DEVICE FOR TRANSPORTATION, SEPARATION AND ORIENTATION OF CUVETTES

(71) Applicant: STRATEC Biomedical AG, Birkenfeld (DE)

(72) Inventor: Alexander Sachs, Roermerberg (DE)

(73) Assignee: STRATEC Biomedical AG, Birkenfeld (DE)

( * ) Notice: Subject to any disclaimer, the term of this patent is extended or adjusted under 35 U.S.C. 154(b) by 0 days.

(21) Appl. No.: 14/825,512

(22) Filed: Aug. 13, 2015

(65) Prior Publication Data

US 2016/0083195 A1 Mar. 24, 2016

(30) Foreign Application Priority Data

Sep. 22, 2014 (GB) .................................. 1416687.0

(51) Int. Cl.
| | |
|---|---|
| *B65G 33/04* | (2006.01) |
| *B65G 47/24* | (2006.01) |
| *G01N 35/04* | (2006.01) |
| *B65G 47/14* | (2006.01) |

(52) U.S. Cl.
CPC ......... *B65G 33/04* (2013.01); *B65G 47/1471* (2013.01); *B65G 47/24* (2013.01); *G01N 35/04* (2013.01); *G01N 2035/0406* (2013.01); *G01N 2035/0487* (2013.01)

(58) Field of Classification Search
CPC .... B65G 47/1471; B65G 33/04; B65G 47/24; B65G 47/1428; B65G 47/1457; B65G 47/256; B65G 2201/0247; G01N 35/04; G01N 2035/0487; G01N 2035/0406
See application file for complete search history.

(56) References Cited

U.S. PATENT DOCUMENTS

| | | | | |
|---|---|---|---|---|
| 3,026,991 A | * | 3/1962 | Kinsley ................. | B65G 33/04 198/459.4 |
| 3,815,730 A | * | 6/1974 | Zwiep ................ | B65G 47/1428 198/389 |
| 4,099,621 A | * | 7/1978 | Dullinger ............... | B65G 33/04 209/522 |
| 4,763,772 A | * | 8/1988 | Gradoboev ........ | B65G 47/1471 198/398 |
| 4,944,382 A | * | 7/1990 | Gradoboev ............ | B65G 47/24 198/399 |
| 5,341,918 A | * | 8/1994 | Covert .................. | B65G 33/04 198/467.1 |
| 5,957,264 A | * | 9/1999 | Carey ....................... | B08B 5/02 198/402 |

(Continued)

FOREIGN PATENT DOCUMENTS

| | | |
|---|---|---|
| EP | 2642300 A1 | 9/2013 |
| JP | 2012176816 A | 9/2012 |

*Primary Examiner* — Mark A Deuble
(74) *Attorney, Agent, or Firm* — 24IP Law Group; Timothy R DeWitt

(57) ABSTRACT

The invention relates to a device, a system and a method for transportation, separation and orientation in a head up position of cuvettes. The invention also relates to using the device or the system for transportation, separation and orientation in head up position of the cuvettes. The device comprises a pipe, a rotating auger, a motor, a guiding plate and a slide rail. The system further comprises at least one cuvette.

17 Claims, 6 Drawing Sheets

(56) References Cited

U.S. PATENT DOCUMENTS

| | | | | |
|---|---|---|---|---|
| 6,053,303 | A | * | 4/2000 | Wang ................... B65G 33/06 198/778 |
| 9,409,723 | B2 | * | 8/2016 | Seidl .................... B65G 37/00 |
| 2008/0226763 | A1 | * | 9/2008 | Charpentier ............. B07C 5/02 425/534 |
| 2012/0055756 | A1 | | 3/2012 | Reardon |

* cited by examiner

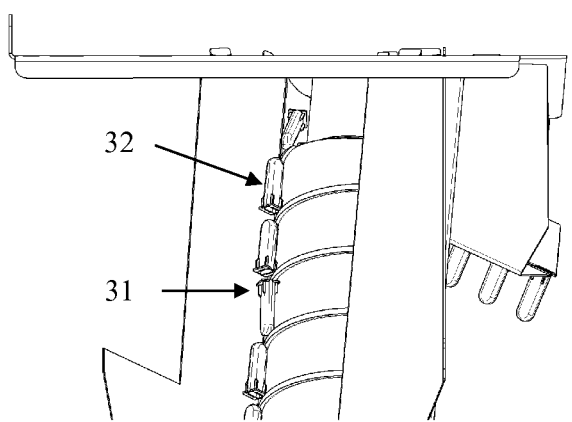
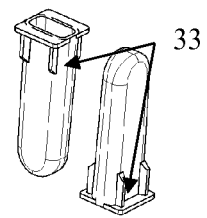
Fig. 3A
Fig. 3B

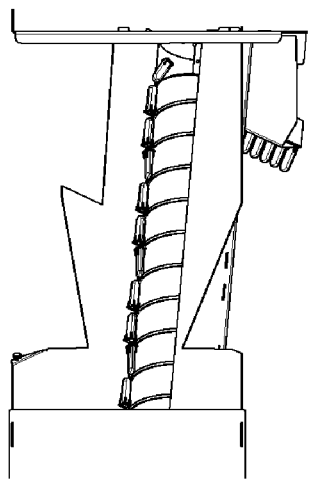 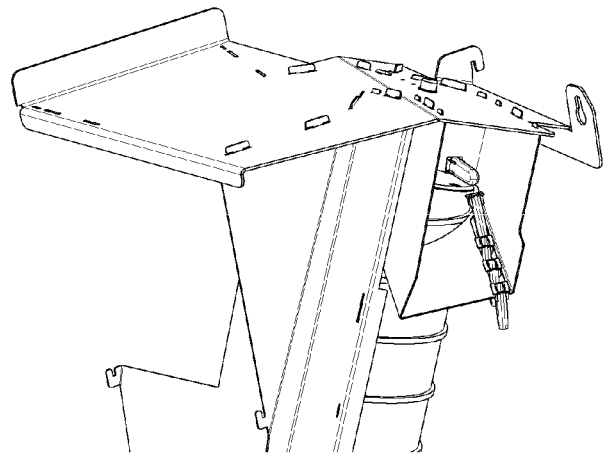
Fig. 5A                              Fig. 5B

DEVICE FOR TRANSPORTATION, SEPARATION AND ORIENTATION OF CUVETTES

CROSS-REFERENCE TO RELATED APPLICATIONS

The present application claims priority of British Patent Application No. GB 1416687.0 filed on Sep. 22, 2015. The aforementioned application is hereby incorporated by reference in its entirety.

BACKGROUND OF THE INVENTION

Field of the Invention

The invention relates to a device, a system and a method for transportation, separation and orientation in a head up position of cuvettes. The invention also relates to using the device or the system for transportation, separation and orientation in head up position of the cuvettes.

Brief Description of the Related Art

When cuvettes are transported from a bulk to a fully automated analyzer system, the fully automated analyzer system requires that the cuvettes are separated as well as orientated in a head up position. Therefore, a device that is to be set up between a bulk of cuvettes and the fully automated analyzer system has to fulfil three major functions: transportation of cuvettes, separation of cuvettes and orientation of cuvettes.

In cuvette loading modules of the state of the art, several modules are necessary which transport, separate or orientate the cuvettes in order to provide the fully automated analyzer system with the cuvettes. Typically, modules like chains, apron conveyers or belts are used to transport the cuvettes. Further, sub modules are necessary, for example an oscillating bowl or sliding profiles to separate and orientate the cuvettes.

Cuvette loading modules of the state of the art are very complex because they contain many components. Such loading modules are expensive and maintenance intensive. Often, the loading modules require several drives, motors and moveable parts, which need to harmonize to each other. This in turn often causes transport jams during the operation of the loading module.

EP 2 642 300 A1 discloses an embodiment of a transport system configured to transport a receptacle which accommodates an upright sample holder containing a sample, characterized by comprising, a screw comprising a rotatable shaft disposed along a predetermined transport path and a helical ridge protruding outward from an outer peripheral surface of the shaft, and a drive unit configured to rotate the screw. The device disclosed in this document is suitable for transporting a receptacle, but not for orientating receptacles that are present in various orientations.

In JP 201217816 A is a container delivery device disclosed including a screw 2 having a spiral groove that is formed at an equal pitch and which holds and conveys a syringe in the groove. Upper and lower elevating and lowering guides 30 and 32 guide the side surface of the syringe that is held in the groove of the screw. The device disclosed in this document is suitable for transporting a receptacle, but not for orientating receptacles that are present in various orientations.

Document US 2012/055756 A1 discloses an apparatus for sorting vials and small containers. The apparatus of this document comprises at least one auger with a plurality of top recesses and a plurality of side recesses. Vials are placed into the apparatus and fall into the top recesses. As vials fall into the top recesses, the vials are transported through the apparatus by the rotation of the auger. If a vial does not fall into a top recess, it is diverted to a top recess, or to an agitation conveyor that transports the vial to a diverter to be diverted back to an auger. Vials within the top recesses are ejected into vertical alignment so that the vials are sorted and oriented properly for packaging The devices disclosed in the prior art comprise complex mechanical components are not suitable for orientating cuvettes for instance in a desired orientation. Thus, there is a need for such a device.

SUMMARY OF THE INVENTION

It is therefore an object of the present invention to provide a device for transportation, separation and orientation in head up position of cuvettes, wherein the device contains fewer parts than the loading modules of the prior art. It is also an object of the present invention to provide a system and a method for transportation, separation and orientation in a head up position of cuvettes.

A device for transportation, separation and orientation in a head up position of cuvettes is provided, wherein the device comprises a pipe, a rotating auger, a motor, a guiding plate and a slide rail.

The guiding plate may be arranged parallel to the rotating auger.

The rotating auger may comprise a core diameter and a thread flank diameter and the thread flank diameter may be larger than the core diameter, and a centre of gravity of a cuvette in a head up or head down position which is to be hold and thereby transported lies within the rotating auger.

A system is further provided for transportation, separation and orientation in a head up position of cuvettes, which comprises the above device and further at least one cuvette.

The at least one cuvette may comprise a head part and a bottom part and the head part of the cuvette may comprise an opening and a rim at least partially surrounding the opening, wherein the rim extends over the opening at least on two opposite sides of opening so that the head part of the cuvette has a greater outer width than the bottom part of the cuvette. The rotating auger of the system comprises at least one pitch and at least one coil and the length of the at least one pitch is at least the length of the cuvette.

The at least one pitch may be angled with respect to the at least one coil.

In one aspect, the opening has a rectangular shape.

The system may further comprise at least one of a filling funnel and a sub module.

In one aspect, the slide rail comprises two parallel rails and the distance between the two parallel rails is smaller than the outer width of the head part of the cuvette.

A method for transportation, separation and orientation in a head up position of cuvettes is provided, wherein the method comprises the following steps:
a. picking up at least one cuvette by a rotating auger from a multitude of cuvettes;
b. separating the at least one cuvette that was picked up from the multitude of cuvettes;
c. transporting the at least one cuvette in a head up or head down position along a longitudinal axis of the rotating auger to a slide rail, wherein while rotating with the rotating auger the cuvettes are pushed towards a guiding plate; and
d. orientating the at least one cuvette in a head up position in the slide rail.

In another aspect, the at least one cuvette is transported through a pipe from the rotating auger to the slide rail and further from the slide rail to a sub module.

The cuvettes, which are not transported in a head up or head down position, may fall back into the multitudes of cuvettes.

The cuvettes, which are not transported in a head up or head down position may fall back by the use of wipers or compressed air.

In one aspect, the multitude of cuvettes is present in a filling funnel.

Use of the device, the system or the method is provided for transportation, separation and orientation in head up position of cuvettes.

BRIEF DESCRIPTION OF THE FIGURES

For a more complete understanding of the instant invention and the advantages thereof, reference is now made to the following description and the accompanying drawing, in which:

FIGS. 3A and 3B illustrate the cuvette in a head down and head up position.

FIGS. 5A and 5B show the upper area of the device according to the present invention.

DETAILED DESCRIPTION OF THE INVENTION

The invention will now be described in detail. Drawings and examples are provided for better illustration of the invention. It will be understood that the embodiments and aspects of the invention described herein are only examples and do not limit the protector's scope of the claims in any way. The invention is defined by the claims and their equivalents. It will be understood that features of one aspect or embodiment of the invention can be combined with the feature of a different aspect or aspects and/or embodiments of the invention.

A device for transportation, separation and orientation in a head up position of cuvettes is provided, wherein the device comprises a pipe, a rotating auger, a motor, guiding plate and a slide rail. This device has the advantage that it does not comprise many components. Therefore, the device is not complex, the device is inexpensive and the device requires low maintenance. Transport jams during the operation of the device can be avoided. The motor may be a single motor. The device can fulfil three major functions within one and the same device: transportation, separation and orientation in a head up position of cuvettes.

Figure 1:
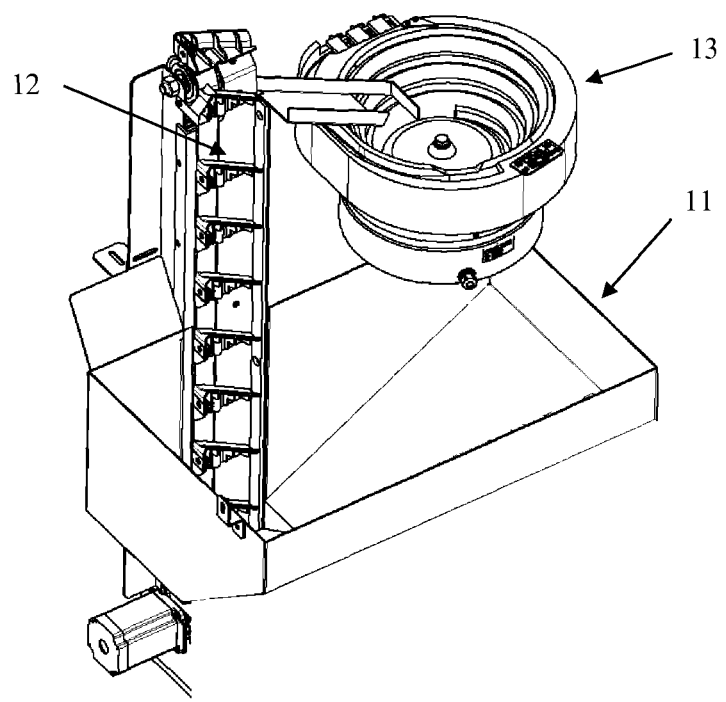
FIG. 1 shows a cuvette loading module of the state of the art.

In contrast, cuvette loading modules of the state of the art usually contain many components. Such a cuvette loading module of the state of the art is illustrated in FIG. 1. FIG. 1 shows a filling funnel 11, which comprises the cuvettes that are to be transported. A transport chain 12 is shown which transports the cuvettes from the filling funnel to an oscillating bowl 13. The oscillating bowl is necessary to separate and orientate the cuvettes. In such a cuvette loading module, two components are thus required to transport, separate and orientate the cuvettes: a transport chain and an oscillating bowl.

Figure 2:
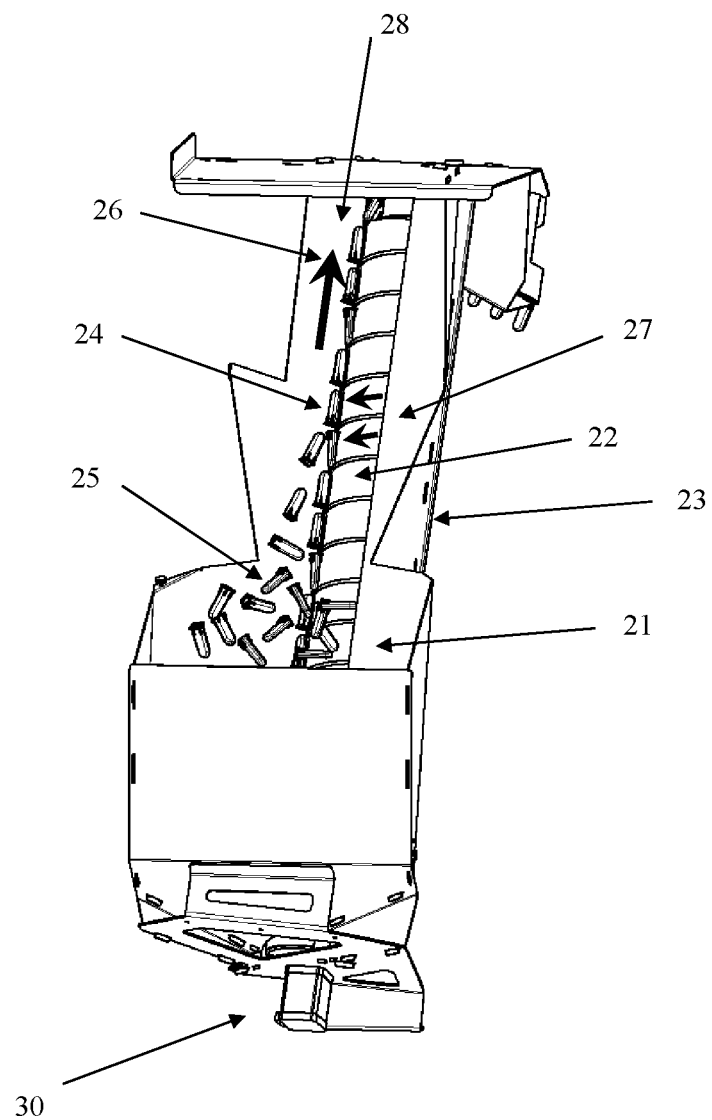
FIG. 2 shows a device according to the present invention for transportation, separation and orientation in a head up position of cuvettes.

The present invention, however, avoids the requirement of too many components and provides a device which can transport, separate and orientate cuvettes within one device. FIG. 2 represents such a device for transportation, separation and orientation in a head up position of cuvettes according to the present invention.

In FIG. 2, the cuvettes are present in a filling funnel 21 as bulk material. An auger 22 transports the cuvettes along a guiding plate 28 of a pipe 23. The cuvettes are hold by the rotating auger 22 and thereby transported upwards, i. e. away from the filling funnel 21. At the same time, the cuvettes are orientated in head up or head down position. Head up or head down position of the cuvettes means that the cuvettes are orientated perpendicular to the diameter of the auger, i. e. the axis connecting the head part of a cuvette and the bottom part of a cuvette is perpendicular to the core diameter of the auger. Cuvettes have an opening which is determined as the head part of the cuvette. Head up position of the cuvette therefore means that the head part of the cuvette is closer to the upper area of the device and the bottom part of the cuvette is closer to the lower part of the device. Head down position of the cuvette in turn means that the bottom part of the cuvette is closer to the upper area of the device and the head part of the cuvette is closer to the bottom area of the device. Incorrectly orientated cuvettes 25 fall back down into the filling funnel 21. Incorrectly orientated means that the cuvettes are not orientated in a head up or head down position. The arrow 26 shows the transport direction of the cuvettes. The arrow 27 shows the rotation direction of the auger. A guiding plate 28, which may be arranged parallel to the rotating auger, guides the cuvettes from the filling funnel along the transport direction 26 upwards. The guiding plate thereby ensures that the cuvettes are transported upwards in a vertical direction. Without a guiding plate, the cuvettes would only rotate with the rotating auger but not transported upwards. In the upper area of the pipe the cuvettes will be transported to a slide rail. The slide rail ensures orientation of the cuvettes in a head up position. The device of FIG. 2 only requires one rotating auger 22. The cuvettes may further be transported to a sub module.

It is to be noted that a filling funnel is not an essential component of the device. FIG. 2 merely demonstrates one example where the cuvettes are present in a filling funnel 21. The rotating auger 22 can pick up cuvettes from a multitude or bulk of cuvettes and it is irrelevant where the multitude or bulk of cuvettes is placed.

A system for transportation, separation and orientation in a head up position of cuvettes is also provided. The system comprises the device as disclosed above and further at least one cuvette. One example of a cuvette that can be transported, separated and orientated by the device as disclosed above and which can be comprised in the system comprises a head part and a bottom part and the head part of the cuvette comprises an opening and a rim at least partially surrounding the opening, wherein the rim extends over the opening at least on two opposite sides of the opening so that the head part of the cuvette has a greater outer width than the bottom part of the cuvette. Such a cuvette is for example shown in FIG. 3B. In one aspect, the opening may have a rectangular shape which is also shown in FIG. 3B. However, the person ordinarily skilled in the art will be aware that other shapes of the opening are also possible.

FIGS. 3A and 3B also illustrate the head up 31 and head down 32 orientation of a cuvette. FIG. 3B shows the head of the cuvette 33. The interaction between the rotating auger and the pipe only allows transportation in two orientations of the cuvettes, that is head up or head down. Cuvettes in all of the other orientations will not be transported because they fall back down into the filling funnel (or any other place where the multitude or bulk of cuvettes is placed). The thread flank shape of the auger determines whether the cuvettes will be hold in one of the two orientations (head up 31 or head down 32 position) or whether the cuvettes will fall back into the filling funnel (or any other place where the multitude or bulk of cuvettes is placed).

Figure 4:
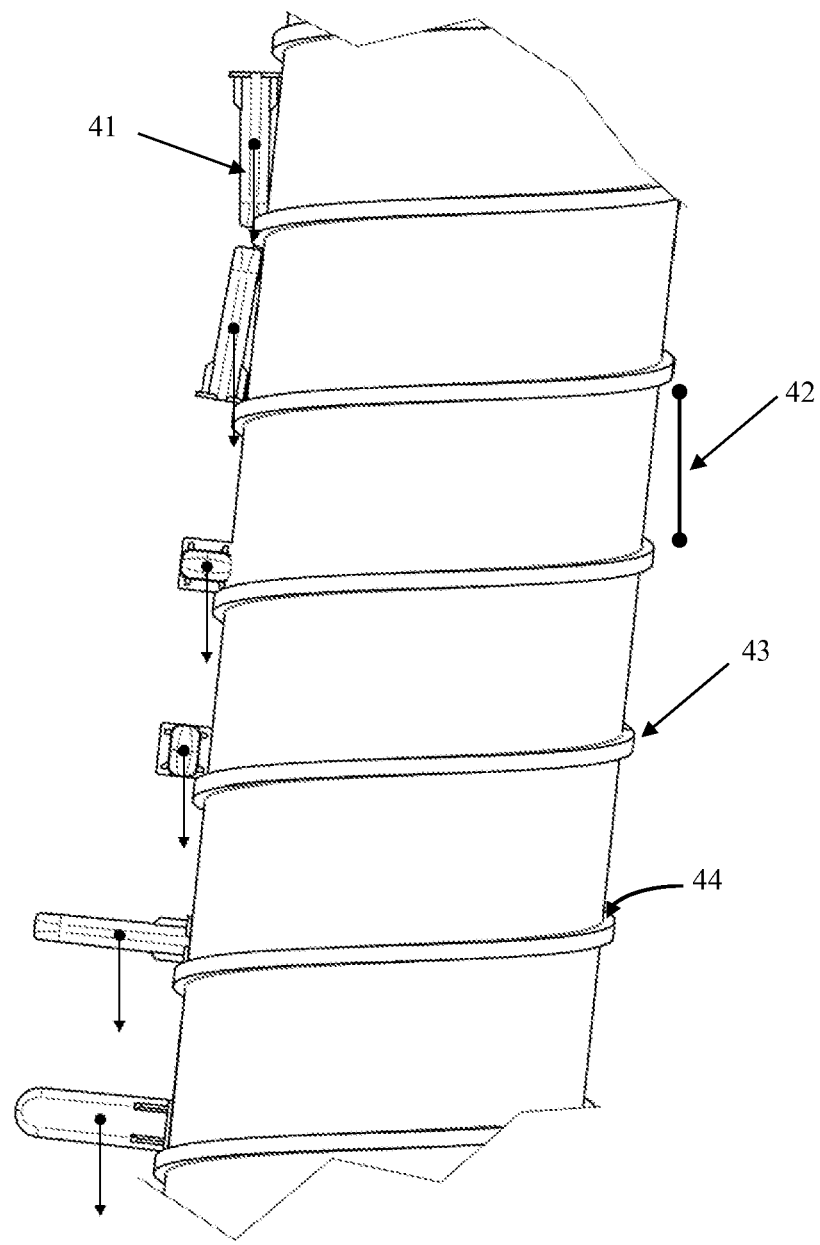
FIG. 4 shows cuvettes being transported by a rotating auger in a head up or head don position.

FIG. 4 also illustrates why the cuvettes can only be transported in a head up or head down position. The arrow 41 represents the centre of gravity of each cuvette. The centre of gravity has to lie within the rotating auger so that the cuvettes are transported and do not fall back down. It is obvious from FIG. 4 that the centre of gravity of the cuvettes lies within the rotating auger as long as the cuvettes are in a head up or head down position. This is the case with the upper two cuvettes. The upper two cuvettes are in a head up and head down position, respectively, and their respective centre of gravity lies within the rotating auger. The slide rail ensures that all cuvettes are finally orientated in a head up position. Therefore, the device allows transportation, separation and orientation in a head up position of cuvettes.

A different cuvette would require different diameters of the pipe, of the core diameter of the auger and of the thread flank diameter of the auger. The design of the cuvette and the design of the device therefore have to be coordinated. The rotating auger comprises at least one pitch 42 and at least one coil 43 as illustrated in FIG. 4. A pitch 42 is the distance between two coils 43. The length of the at least one pitch 42 is at least the length of the cuvette. The at least one pitch 42 may be angled with respect to the at least one coil 43. The rotating auger itself may also be angled. The coil 43 of the rotating auger further exhibits an upper edge 44, wherein the width of the upper edge 44 can be defined as one half of the difference between the thread flank diameter and the core diameter of the rotating auger. There is an interrelationship between the width of the upper edge 44 and the angle of the pitch 42 or the angle of the rotating auger. The more angled the pitch 42 or the rotating auger, the less width of the upper edge 44 is required for the cuvettes to be hold in place.

The system may further comprise at least one of a filling funnel and a sub module.

The filling funnel may be of any shape which allows a multitude or bulk of cuvettes to be stored and to be picked up from the auger for transportation, separation and orientation. As discussed above, the multitude or bulk of cuvettes does not need to be placed in a filling funnel.

FIGS. 5A and 5B show the upper part of the device or of the system, where the cuvettes pass through specific edges so as to then be transported into a slot of a slide rail. The cuvettes are then transported to a sub module. The system may comprise the sub module. FIG. 5A shows the auger transporting cuvettes in a head up or head down position which have been separated. In the upper right part of FIG. 5A cuvettes hanging in a slide rail are shown. In FIG. 5B the upper part of the device or of the system is shown from a different perspective. The cuvettes pass through specific edges from the auger to the slide rail and are hanging in the slide rail from where they can be transported to a sub module.

Figures 6A, 6B:
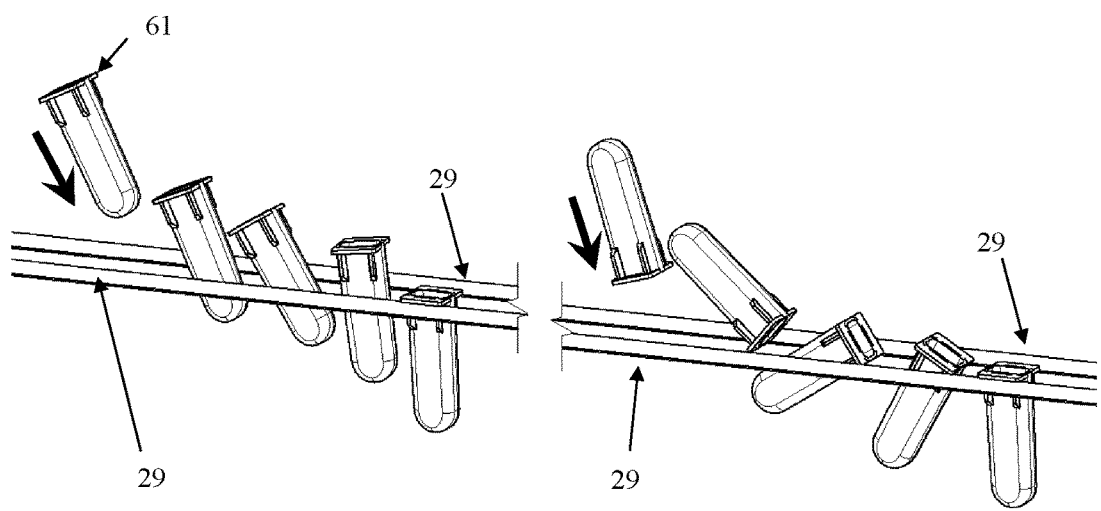
FIGS. 6A and 6B show a slide rail and cuvettes.

The slide rail may comprise two parallel rails and the distance between the two parallel rails is smaller than the outer width of the head part of the cuvette. FIGS. 6A and 6B shows a schematic illustration of such a slide rail. The cuvettes will arrive at the slide rail from the upper area of the device or of the system and either be in a head up or head down position. FIG. 6A shows that the cuvettes arrive in a head up position and FIG. 6B shows that the cuvettes arrive in a head down position. The sub module or any fully automated analyzer system that the cuvettes can be transported to eventually require the cuvettes in a head up position so that they can be filled with liquid. The schematic illustration in FIG. 6 shows how and why both orientations head up and head down can be used to transport the cuvettes to the slide rail. The cuvette comprises an opening and a rim 61 at least partially surrounding the opening. The rim of the cuvette 61 extends over the opening at least on two opposite sides of the opening so that the head part of the cuvette has a greater outer width than the bottom part of the cuvette. Such a cuvette assures that the cuvette will fall down into the slot of the slide rail in a head up position and eventually all cuvettes will be in a head up position.

A method for transportation, separation and orientation in a head up position of cuvettes is also provided. The method comprises the following steps:
 a. picking up at least one cuvette by a rotating auger from a multitude of cuvettes,
 b. separating the at least one cuvette that was picked up from the multitude of cuvettes;
 c. transporting the at least one cuvette in a head up or head down position along a longitudinal axis of the rotating auger through a pipe to a slide rail, wherein while rotating with the rotating auger the cuvettes are pushed towards a guiding plate,
 d. orientating the at least one cuvette in a head up position in the slide rail.

The method is best illustrated by the above disclosed FIG. 2. The auger rotates in one direction and thereby allows picking up at least one cuvette from a multitude of cuvettes. A multitude of cuvettes means at least two cuvettes and is synonymous with a bulk of cuvettes. The longitudinal axis of the rotating auger refers to the axis perpendicular to the diameter of the auger. The diameter of the auger comprises an inner (core) and an outer (thread flank) diameter as disclosed above.

Cuvettes, as disclosed above, which are not transported in a head up or head down position fall back into the multitude of cuvettes. They may fall back by the use of wipers or compressed air. However, other methods to aid the incorrectly orientated cuvettes to fall back into the multitude of cuvettes may also be possible.

The multitude of cuvettes may be present in a filling funnel from where the auger picks up the at least one cuvette from the multitude of cuvettes. The person ordinarily skilled in the art will understand that other means for storing the cuvettes are also possible.

It has become obvious from above disclosures and figures that the device and the system can be used for transportation, separation and orientation in a head up position of cuvettes. The device and the system are not complex and are of low maintenance. They may require only a single motor which reduces the number of components. No further sub modules for separation or orientation of the cuvettes are required because the device is able to fulfil all three functions of transporting the cuvettes, separating the cuvettes and orientating the cuvettes within one device.

In contrast to the devices disclosed in the prior art, the device of the instant invention is based on an combination of an angled auger and a slide rail ensuring that cuvettes will be in a head up position after entering the slide rail. The number of mechanical components is thus reduced.

The device disclosed in document US 2012/055756 A1 is an example of a device known from prior art that comprises complex mechanical parts. The device comprises two augers instead of only one auger in addition to several other mechanical parts for transporting closed vessels. However, the device of US 2012/055756 is not only structurally different, but also not suitable for orientating open receptacles like cuvettes or reaction vessels in automated analyser systems.

REFERENCE NUMERALS

11 Filling funnel
12 Transport chain
13 Oscillating bowl
21 Filling funnel
22 Auger
23 Pipe
24 Separation of the cuvettes along a guiding plate
25 Incorrectly orientated cuvettes
26 Transport direction of the cuvettes
27 Rotation direction of the auger
28 Guiding plate
31 Head up position of the cuvette
32 Head down position of the cuvette
33 Head of the cuvette
41 Centre of gravity of each cuvette
42 Pitch
43 Coil
44 Upper edge of the coil
61 Rim of the cuvette

What is claimed is:

1. A device for transportation, separation and orientation of cuvettes in a head up position, the device comprising a motor connected to and for rotating, a vertical orientated auger located inside a pipe with a guiding plate that is arranged parallel to the auger, wherein the rotating auger comprises a core diameter and a thread flank diameter and the thread flank diameter is larger than the core diameter, and wherein a centre of gravity of a cuvette in a head up or head down position which is to be hold and thereby transported by the auger lies within the thread flank diameter and a slide rail with two parallel rails with a distance to one another being smaller than the outer width of a head part of the cuvette is arranged in the upper area of the pipe for taking up the cuvettes in a head up position.

2. A system for transportation, separation and orientation of cuvettes in a head up position, the system comprising the device according to claim 1 and further comprising at least one cuvette, wherein the cuvette comprises a head part and a bottom part and the head part of the cuvette comprises an opening and a rim at least partially surrounding the opening, wherein the rim extends over the opening at least on two opposite sides of the opening so that the head part of the cuvette has a greater outer width than the bottom part of the cuvette, and wherein the rotating auger comprises at least one pitch and at least one coil and the length of the at least one pitch is at least the length of the cuvette.

3. The system according to claim 2, wherein the at least one pitch is angled with respect to the at least one coil.

4. The system according to claim 2, wherein the opening of the cuvette has a rectangular shape.

5. The system according to claim 2, wherein the system further comprises at least one of a filling funnel and a sub module.

6. The device of claim 1, wherein the rotating auger comprises at least one pitch and at least one coil and the length of the at least one pitch is at least the length of the cuvette.

7. The device of claim 6, wherein the at least one pitch is angled with respect to the at least one coil.

8. The device of claim 1, wherein the head part of the cuvette comprises an opening and a rim at least partially surrounding the opening, wherein the rim extends over the opening at least on two opposite sides of the opening so that the head part of the cuvette has a greater outer width than the bottom part of the cuvette.

9. The device of claim 8, wherein the opening of the cuvette has a rectangular shape.

10. A method for transportation, separation and orientation of cuvettes in a head up position, the method comprising the following steps:
picking up at least one cuvette by a vertical orientated rotating auger located inside a pipe with a guiding plate that is arranged parallel to the rotating auger that is connected to a motor for rotating it, wherein said rotating auger comprises a core diameter and a thread flank diameter and the thread flank diameter is larger than the core diameter, and wherein a centre of gravity of a cuvette in a head up or head down position which is to be hold and thereby transported by the auger lies within the within the thread flank diameter from a multitude of cuvettes,
separating the at least one cuvette that was picked up from the multitude of cuvettes; and
transporting the at least one cuvette in a head up or head down position along a longitudinal axis of the rotating auger to a slide rail,
wherein while rotating with the rotating auger the cuvettes are pushed towards a guiding plate, and
passing the cuvettes from the rotating auger to the slide rail; and
orientating the at least one cuvette in a head up position in the slide rail with two parallel rails with a distance to one another being smaller than the outer width of a head part of the cuvette is arranged in the upper area of the pipe for taking up the cuvettes in a head up position.

11. The method according to claim 10, wherein the at least one cuvette is transported through a pipe from the rotating auger to the slide rail.

12. The method according to claim 10, wherein the at least one cuvette is further transported from the slide rail to a sub module.

13. The method according to claim 10, wherein cuvettes, which are not transported in a head up or head down position fall back into the multitude of cuvettes.

14. The method according to claim 13, wherein cuvettes, which are not transported in a head up or head down position fall back by the use of wipers or compressed air.

15. The method according to claim 10, wherein the multitude of cuvettes is present in a filling funnel.

16. A method for transportation, separation and orientation of cuvettes in a head up position comprising the step of
using a device comprising a motor connected to and for rotating a vertical orientated auger located inside a pipe with a guiding plate that is arranged parallel to the auger, wherein the rotating auger comprises a core diameter and a thread flank diameter and the thread flank diameter is larger than the core diameter, and wherein a centre of gravity of a cuvette in a head up or head down position which is to be hold and thereby transported by the auger lies within the within the thread flank diameter and a slide rail with two parallel rails with a distance to one another being smaller than the outer width of a head part of the cuvette is arranged in the upper area of the pipe for taking up the cuvettes in a head up position.

17. A method for transportation, separation and orientation in a head up position of cuvettes comprising the step of using a system for transportation, separation and orientation of cuvettes in a head up position, the system comprising a device a device comprising a motor connected to and for rotating a vertical orientated auger located inside a pipe with a guiding plate that is arranged parallel to the auger, wherein the rotating auger comprises a core diameter and a thread flank diameter and the thread flank diameter is larger than the core diameter, and wherein a centre of gravity of a cuvette in a head up or head down position which is to be hold and thereby transported by the auger lies within the within the thread flank diameter and a slide rail with two parallel rails with a distance to one another being smaller than the outer width of a head part of the cuvette is arranged in the upper area of the pipe for taking up the cuvettes in a head up position; and at least one cuvette, wherein the cuvette comprises a head part and a bottom part and the head part of the cuvette comprises an opening and a rim at least partially surrounding the opening, wherein the rim extends over the opening at least on two opposite sides of the opening so that the head part of the cuvette has a greater outer width than the bottom part of the cuvette, and wherein the rotating auger comprises at least one pitch and at least one coil and the length of the at least one pitch is at least the length of the cuvette.

* * * * *